(12) United States Patent
Whipple et al.

(10) Patent No.: US 11,439,809 B2
(45) Date of Patent: Sep. 13, 2022

(54) SYSTEMS, DEVICES, AND METHODS FOR OVARIAN DENERVATION

(71) Applicant: COVIDIEN LP, Mansfield, MA (US)

(72) Inventors: Dale E. Whipple, Nashua, NH (US); Mireille K. Akilian, Candia, MA (US); Nikolai D. Begg, Wayland, MA (US); Chad A. Pickering, Woburn, MA (US)

(73) Assignee: Covidien LP, Mansfield, MA (US)

( * ) Notice: Subject to any disclaimer, the term of this patent is extended or adjusted under 35 U.S.C. 154(b) by 315 days.

(21) Appl. No.: 16/121,582

(22) Filed: Sep. 4, 2018

(65) Prior Publication Data

US 2019/0083164 A1    Mar. 21, 2019

Related U.S. Application Data

(60) Provisional application No. 62/561,601, filed on Sep. 21, 2017.

(51) Int. Cl.
*A61N 1/05*    (2006.01)
*A61N 7/02*    (2006.01)
(Continued)

(52) U.S. Cl.
CPC .............. *A61N 1/0524* (2013.01); *A61B 8/12* (2013.01); *A61B 17/32* (2013.01); *A61B 17/320068* (2013.01); *A61B 18/0206* (2013.01); *A61B 18/042* (2013.01); *A61B 18/14* (2013.01); *A61B 18/1485* (2013.01); *A61B 18/1492* (2013.01); *A61B 18/1815* (2013.01); *A61M 29/02* (2013.01); *A61N 1/0521* (2013.01); *A61N 1/44* (2013.01); *A61N 5/022* (2013.01); *A61N 7/022* (2013.01); *A61B 17/22012* (2013.01);
(Continued)

(58) Field of Classification Search
CPC ......... A61B 8/12; A61B 17/32; A61B 8/1815; A61N 1/0521; A61N 1/0524; A61N 1/0551; A61N 1/36007; A61N 1/3605; A61N 1/3606; A61N 1/36107; A61N 1/36167
See application file for complete search history.

(56) References Cited

U.S. PATENT DOCUMENTS 6,039,736 A     3/2000   Platt, Jr.
7,623,924 B2 *  11/2009  Narciso, Jr. .......... A61N 1/0556
                                                    607/39
(Continued)

FOREIGN PATENT DOCUMENTS

WO      2016025132 A1    2/2016

OTHER PUBLICATIONS

Lobo, R. A., Gershenson, D. M., Lentz, G. M., Valea, F. A. (2016). Comprehensive Gynecology E-Book. Elsevier. Retrieved 2020. (Year: 2016).*

(Continued)

*Primary Examiner* — Daniel W Fowler
*Assistant Examiner* — Annie L Patton
(74) *Attorney, Agent, or Firm* — Carter, DeLuca & Farrell LLP

(57) ABSTRACT

Methods for effectuating ovarian denervation include advancing a disruptor intravaginally to access an ovarian nerve and applying the disruptor to the ovarian nerve to denervate the ovarian nerve to limit ovarian sympathetic neural activity and control hormonal secretion.

12 Claims, 14 Drawing Sheets

(51) Int. Cl.

| | | |
|---|---|---|
| *A61B 8/12* | (2006.01) | |
| *A61B 17/32* | (2006.01) | |
| *A61B 18/04* | (2006.01) | |
| *A61B 18/14* | (2006.01) | |
| *A61B 18/02* | (2006.01) | |
| *A61B 18/18* | (2006.01) | |
| *A61M 29/02* | (2006.01) | |
| *A61N 1/44* | (2006.01) | |
| *A61N 5/02* | (2006.01) | |
| *A61B 18/00* | (2006.01) | |
| *A61N 1/36* | (2006.01) | |
| *A61B 18/24* | (2006.01) | |
| *A61B 17/22* | (2006.01) | |
| *A61B 17/42* | (2006.01) | |
| *A61B 90/00* | (2016.01) | |
| *A61N 7/00* | (2006.01) | |

(52) U.S. Cl.
CPC ......... *A61B 17/32002* (2013.01); *A61B 17/42* (2013.01); *A61B 18/24* (2013.01); *A61B 2017/22051* (2013.01); *A61B 2017/320008* (2013.01); *A61B 2017/320069* (2017.08); *A61B 2018/00404* (2013.01); *A61B 2018/00434* (2013.01); *A61B 2018/00559* (2013.01); *A61B 2018/00577* (2013.01); *A61B 2018/0212* (2013.01); *A61B 2018/1861* (2013.01); *A61B 2090/3784* (2016.02); *A61M 2205/3368* (2013.01); *A61M 2205/3375* (2013.01); *A61M 2210/1408* (2013.01); *A61N 1/36057* (2013.01); *A61N 1/36062* (2017.08); *A61N 1/36103* (2013.01); *A61N 2007/003* (2013.01)

(56) References Cited

U.S. PATENT DOCUMENTS

| | | | |
|---|---|---|---|
| 8,784,410 B2 | 7/2014 | Dunning | |
| 9,119,650 B2 | 9/2015 | Brannan et al. | |
| 9,247,992 B2 | 2/2016 | Ladtkow et al. | |
| 9,750,568 B2 | 9/2017 | Sobotka | |
| 10,595,936 B2 * | 3/2020 | Zarins | A61B 8/12 |
| 2006/0079943 A1 * | 4/2006 | Narciso | A61N 1/36107 607/39 |
| 2012/0116382 A1 * | 5/2012 | Ku | A61M 25/0138 606/33 |
| 2012/0116416 A1 | 5/2012 | Neff et al. | |
| 2012/0136350 A1 | 5/2012 | Goshgarian et al. | |
| 2013/0116677 A1 * | 5/2013 | Eskuri | A61B 18/1445 606/27 |
| 2013/0317495 A1 | 11/2013 | Brannan | |
| 2014/0250661 A1 | 9/2014 | Vreeman et al. | |
| 2015/0051594 A1 * | 2/2015 | Sobotka | A61B 18/1492 606/21 |
| 2016/0045728 A1 * | 2/2016 | Lockwood | A61N 1/36107 607/39 |
| 2018/0043155 A1 * | 2/2018 | Famm | A61F 7/12 |
| 2018/0110554 A1 * | 4/2018 | Zarins | A61B 18/1485 |

OTHER PUBLICATIONS

Better Health—Menstrual cycle. Menstrual cycle—Better Health Channel, (n.d.). https://www.betterhealth.vic.gov.au/health/conditionsandtreatments/menstrual-cycle. (Year: 2017).*

International Preliminary Report on Patentability and Written Opinion issued in corresponding International Application No. PCT/US2018/051866 dated Apr. 2, 2020, 5 pages.

Notification regarding International Search Report and Written Opinion issued in International Application No. PCT/US2018/051866 dated Jan. 18, 2019.

* cited by examiner

SYSTEMS, DEVICES, AND METHODS FOR OVARIAN DENERVATION

CROSS REFERENCE TO RELATED APPLICATIONS

This application claims the benefit of U.S. Provisional Patent Application No. 62/561,601, filed Sep. 21, 2017, the entire contents of which are incorporated by reference herein.

TECHNICAL FIELD

The present disclosure relates to ovarian denervation and, more particularly, to systems, devices, and methods for disrupting ovarian nerve supply to limit ovarian sympathetic neural activity and control hormonal secretion.

BACKGROUND

Ovarian sympathetic neural activity can cause or exacerbate several ovarian conditions, including common endocrine disorders affecting women of reproductive ages (e.g., 12-45 years old) such as Polycystic Ovary Syndrome (PCOS) and Premenstrual Dysphoric Disorder (PMDD). Scientific literature suggests that ovarian hormonal secretion is regulated by sympathetic nervous activity to the ovary. The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the ovarian SNS has been identified experimentally and in humans as a likely contributor to the complex pathophysiology of PCOS.

SUMMARY

In accordance with an aspect of the present disclosure, a method for effectuating ovarian denervation includes advancing a disruptor intravaginally and through a vaginal fornix to access a position adjacent an ovarian nerve. The method includes activating the disruptor to denervate the ovarian nerve.

The disruptor may include an ablation device, and advancing the disruptor through the vaginal fornix may include advancing the ablation device through the vaginal fornix. Activating the disruptor may include ablating the ovarian nerve with the ablation device.

In certain aspects of the present disclosure, the method may further include advancing an ultrasound probe intravaginally and positioning the ultrasound probe to enable the ultrasound probe to project ultrasound in alignment with an ovary while the disrupter is activated. The disrupter may be coupled to the ultrasound probe, and the disruptor and the ultrasound probe may be introduced intravaginally together. The method may further include advancing the disruptor relative to the ultrasound probe. A guide tube may be coupled to the ultrasound probe; and advancing the disruptor relative to the ultrasound probe may include advancing the disruptor through the guide tube. Advancing the disruptor through the guide tube may include directing the disruptor away from the ultrasound probe as the disruptor is advanced relative to the ultrasound probe. Directing the disruptor away from the ultrasound probe may include intravaginally positioning the guide tube such that the guide tube directs the disruptor toward the vaginal fornix.

In some aspects of the present disclosure, activating the disruptor may disrupt a myelin sheath of the ovarian nerve without disrupting a nerve fiber of the ovarian nerve.

In certain aspects of the present disclosure, activating the disruptor may include applying microwave energy to the ovarian nerve.

In aspects of the present disclosure, activating the disruptor may include applying electrosurgical plasma to the ovarian nerve.

In some aspects of the present disclosure, activating the disruptor may include applying a blade to the ovarian nerve.

According to yet another aspect of the present disclosure, an ovarian denervation system is provided. The ovarian denervation system includes an intravaginal ultrasound probe, a guide tube coupled to the intravaginal ultrasound probe, and a disruptor. The disruptor is advanceable through the guide tube and relative to the intravaginal ultrasound probe. The disruptor is configured to advance through a vaginal fornix to access a position adjacent an ovarian nerve. The disruptor is configured to denervate the ovarian nerve.

In some embodiments of the present disclosure, the disruptor may include an end effector that is configured to ablate the ovarian nerve with microwave energy.

In certain embodiments of the present disclosure, the disruptor may include an end effector that is configured to emit electrosurgical plasma for disrupting the ovarian nerve.

In embodiments of the present disclosure, the disruptor may include a blade that may be configured to scrape the ovarian nerve.

In some embodiments of the present disclosure, the guide tube includes a curved distal portion configured to direct the disruptor toward the vaginal fornix.

In certain embodiments, the disruptor may be configured to disrupt a myelin sheath of a first ovarian nerve without disrupting a nerve fiber of the first ovarian nerve.

According to still another aspect of the present disclosure, a method for effectuating ovarian denervation includes advancing a disruptor intravaginally and through a fundus of a uterus to a position adjacent an ovarian nerve, and activating the disruptor to denervate the ovarian nerve.

In aspects of the present disclosure, the disruptor may include an ablation device, and advancing the disruptor through the fundus includes advancing the ablation device through the fundus.

In some aspects of the present disclosure, the method includes advancing an ultrasound probe intravaginally and positioning the ultrasound probe to project ultrasound in alignment with an ovary while the disrupter is activated. The disrupter may be coupled to the ultrasound probe, and the disruptor and the ultrasound probe may be introduced intravaginally together. The method may further include advancing the disruptor relative to the ultrasound probe. A guide tube may be coupled to the ultrasound probe; and advancing the disruptor relative to the ultrasound probe may include advancing the disruptor through the guide tube. Advancing the disruptor through the guide tube may include directing the disruptor away from the ultrasound probe as the disruptor is advanced relative to the ultrasound probe. Directing the disruptor away from the ultrasound probe may include intravaginally positioning the guide tube such that the guide tube directs the disruptor toward the fundus.

According to yet another aspect of the present disclosure, an ovarian denervation system includes an intravaginal ultrasound probe, a guide tube coupled to the intravaginal ultrasound probe, and a disruptor. The disruptor is advanceable through the guide tube and relative to the intravaginal ultrasound probe. The disruptor is configured to advance through a fundus of a uterus to a position adjacent an ovarian nerve. The disruptor is configured to denervate the ovarian nerve.

In some embodiments of the present disclosure, the guide tube may include a curved distal portion configured to direct the disruptor toward the fundus.

According to still another aspect of the present disclosure, a method for effectuating ovarian denervation includes advancing a disruptor intravaginally and into a fallopian tube to access an ovarian nerve, and activating the disruptor to denervate the ovarian nerve.

In some aspects of the present disclosure, the disruptor may include an ablation device, and advancing the disruptor through the fallopian tube may include advancing the ablation device through the fallopian tube.

In certain aspects of the present disclosure, the method may further include advancing the disruptor to a position adjacent to an infundibulopelvic ligament.

In aspects of the present disclosure, the method may further include advancing an ultrasound probe intravaginally, and positioning the ultrasound probe to project ultrasound in alignment with an ovary while the disrupter is activated. The method may further include advancing the disruptor relative to the ultrasound probe. A guide tube may be coupled to the ultrasound probe, and advancing the disruptor relative to the ultrasound probe may include advancing the disruptor through the guide tube. Advancing the disruptor through the guide tube may include directing the disruptor away from the ultrasound probe as the disruptor is advanced relative to the ultrasound probe. Directing the disruptor away from the ultrasound probe may include intravaginally positioning the guide tube such that the guide tube directs the disruptor toward the uterus.

According to yet another aspect of the present disclosure, an ovarian denervation system includes an intravaginal ultrasound probe, a guide tube coupled to the intravaginal ultrasound probe, and a disruptor. The disruptor is advanceable through the guide tube and relative to the intravaginal ultrasound probe. The disruptor is configured to advance into a fallopian tube to a position adjacent an ovarian nerve. The disruptor is configured to denervate the ovarian nerve.

In some embodiments, the guide tube includes a curved distal portion configured to direct the disruptor toward the fallopian tube.

According to still another aspect of the present disclosure, a method for effectuating ovarian denervation includes introducing a catheter into an ovarian vessel, and expanding a balloon within the ovarian vessel to disrupt an ovarian nerve that extends along the ovarian vessel without tearing a wall of the ovarian vessel.

The method may further include positioning the balloon adjacent an infundibulopelvic ligament that supports the ovarian vessel.

In some aspects of the present disclosure, expanding the balloon may include inflating the balloon with inflation fluid.

In certain aspects of the present disclosure, the method may include deflating the balloon and positioning the balloon within a second ovarian vessel for re-inflation. The method may further include re-inflating the balloon within the second ovarian vessel to disrupt a second ovarian nerve that extends along the second ovarian vessel without tearing a wall of the second ovarian vessel.

In some aspects of the present disclosure, expanding the balloon may include tearing the ovarian nerve that extends along the ovarian vessel without tearing the wall of the ovarian vessel.

According to still another aspect of the present disclosure, a method for effectuating ovarian denervation includes implanting one or more electrodes within an ovarian vessel, and activating the one or more electrodes to disrupt an ovarian nerve.

In some aspects of the present disclosure, the method may further include implanting one or more additional electrodes adjacent to the ovarian vessel. The method may include activating the one or more additional electrodes to disrupt an ovarian nerve. Activating the one or more additional electrodes may include intermittently conducting electrical energy through the one or more additional electrodes. Implanting the one or more additional electrodes may include implanting the one or more additional electrodes adjacent to an infundibulopelvic ligament.

In certain aspects, implanting the one or more electrodes may include implanting the one or more electrodes within an infundibulopelvic ligament. Activating the one or more electrodes may include intermittently conducting electrical energy through the one or more electrodes.

According to yet another aspect of the present disclosure, a method for effectuating ovarian denervation includes implanting one or more electrodes adjacent to an ovarian vessel, and activating the one or more electrodes to disrupt an ovarian nerve.

In some aspects of the present disclosure, implanting the one or more electrodes includes implanting the one or more electrodes adjacent to an infundibulopelvic ligament.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the present systems, devices, and methods for disrupting an ovarian nerve and, together with a general description of the disclosure given above, and the detailed description given below, serve to explain the principles of the disclosure, wherein.

DETAILED DESCRIPTION

Figure 1A:
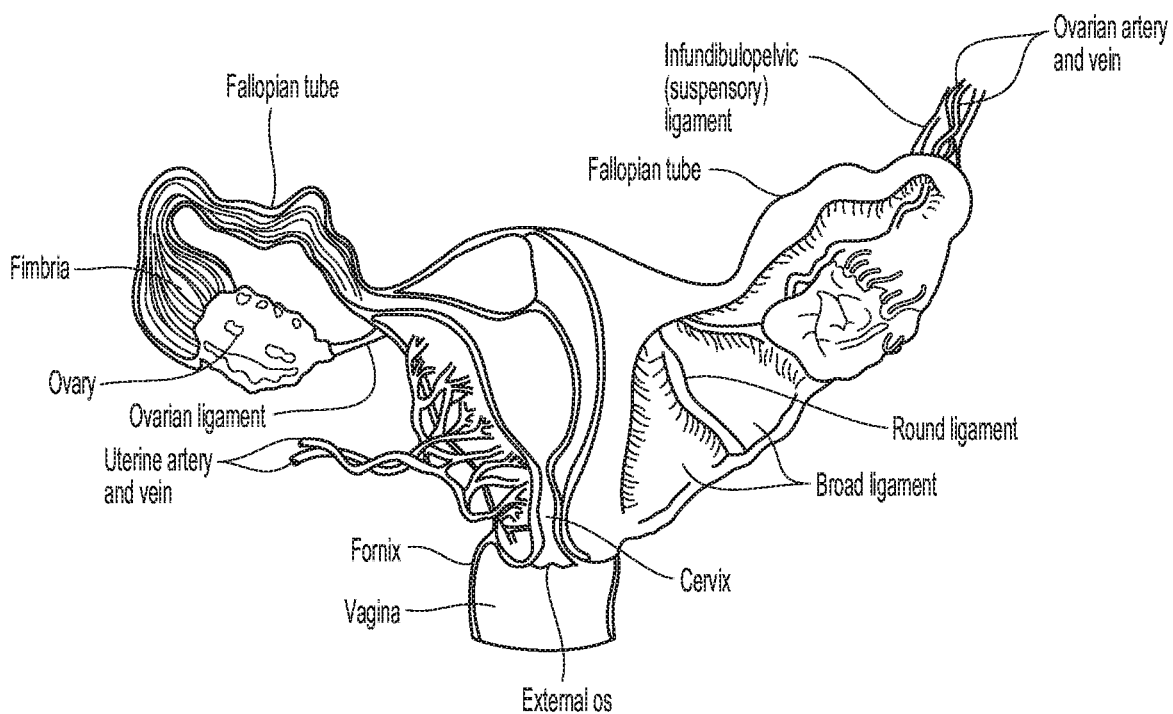
FIGS. 1A and 1B are anatomical views illustrating vaginal tissue.
Figure 1B:
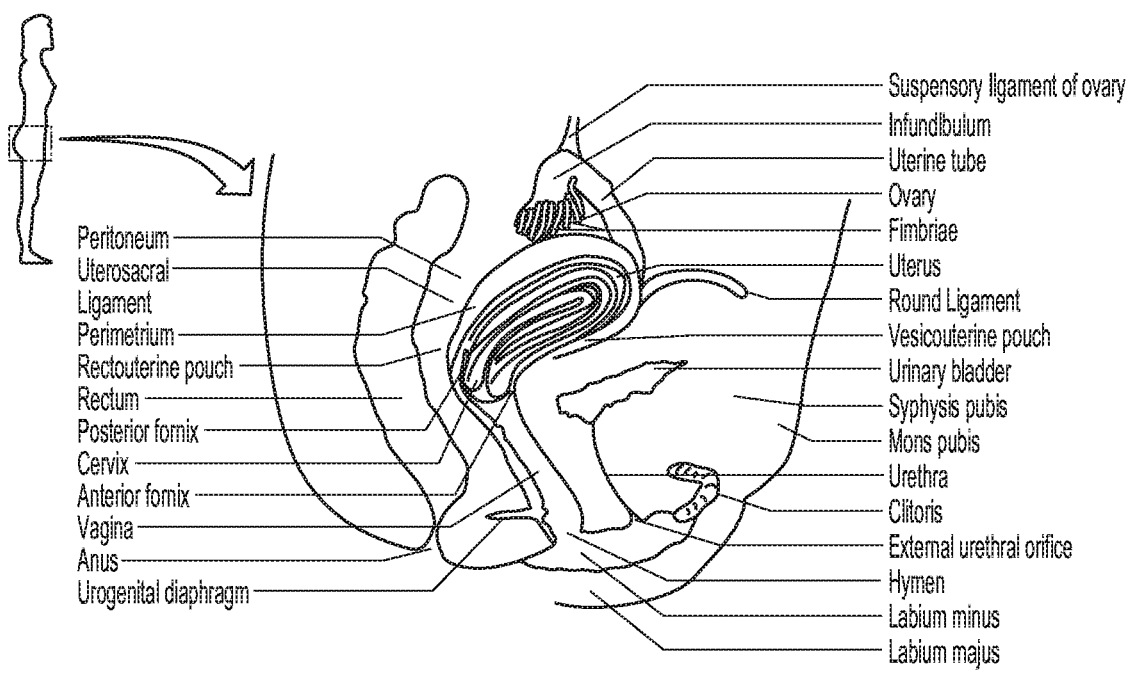

A need exists to provide systems, devices, and/or methods for disrupting nerve supply to an ovary.

Although the presently disclosed systems, devices, methods are described herein with respect to ovarian denervation, these systems, devices, and/or methods may be modified for disrupting the nerve supply to other organs or body systems or to treat other diseases or conditions.

Embodiments of the presently disclosed systems, devices, and/or methods for disrupting ovarian nerve supply are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel. As used herein, the terms "denervation," "disruption" or other similar terms refer to any loss in, or damage to, nerve supply including partial or complete loss of, or damage to, nerve supply.

In the following description, well-known functions or constructions are not described in detail to avoid obscuring the present disclosure in unnecessary detail.

Figure 1C:
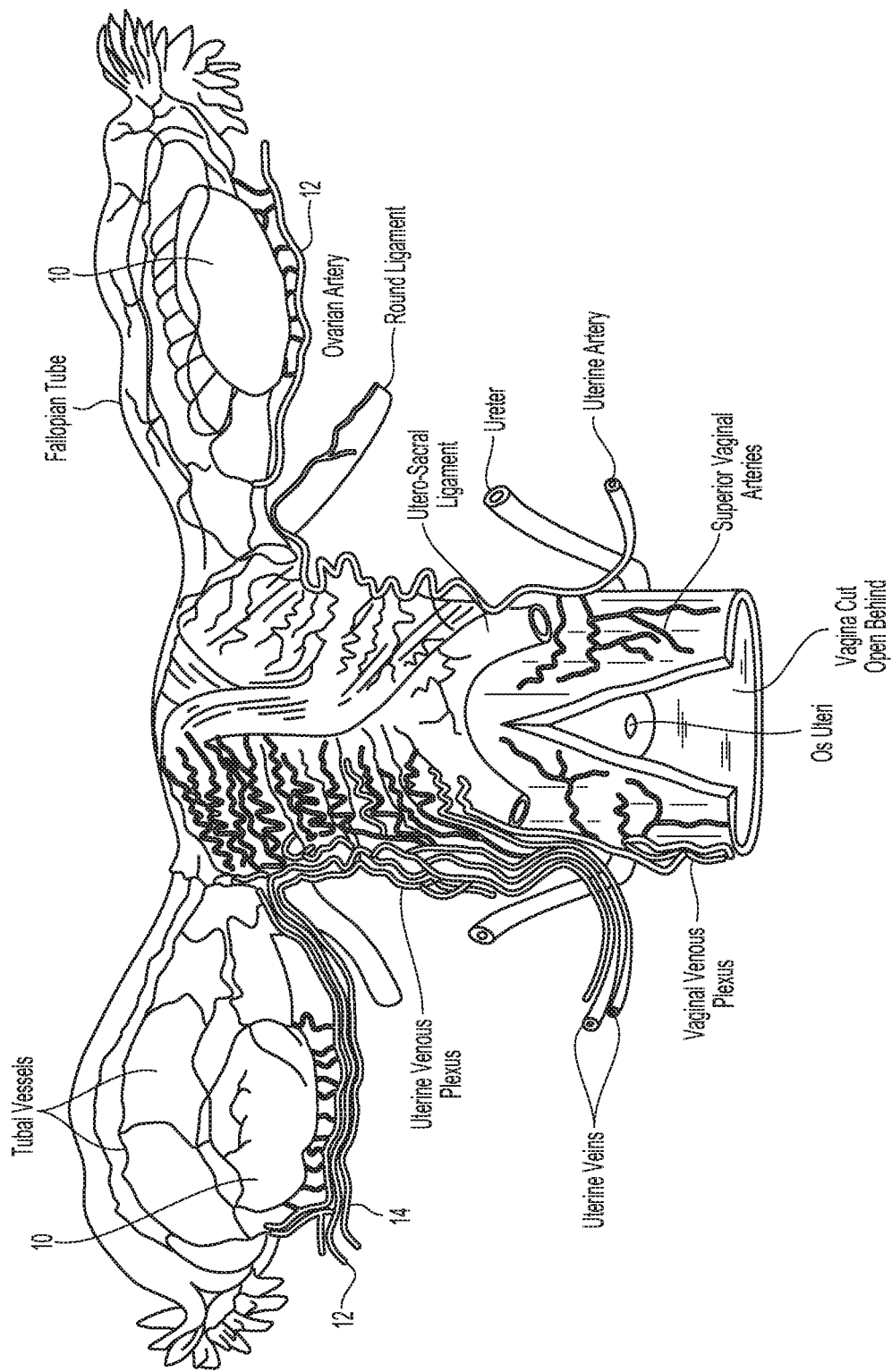
FIG. 1C is an anatomical view illustrating an ovarian artery and nearby organs and vessels.

The vaginal anatomy is generally illustrated in FIGS. 1A-1D. FIG. 1C, in particular, is an anatomical view illustrating the ovaries 10 and nearby organs and vessels, including an ovarian artery 12. Treatment procedures for ovarian denervations or disruptions, in accordance with embodiments of the present technology, can include applying a treatment modality at one or more treatment locations proximate a structure having a relatively high concentration of ovarian nerves. In some aspects, for example, at least one treatment location can be proximate a portion of the ovarian artery 12, a branch of the ovarian artery 12, an ostium of the ovarian artery 12, an ovarian vein 14, a branch of an ovarian vein, an ostium of an ovarian vein, and/or another suitable structure (e.g., another suitable structure extending along the suspensory ligament) in the vicinity of ovarian nerves.

Figure 1D:
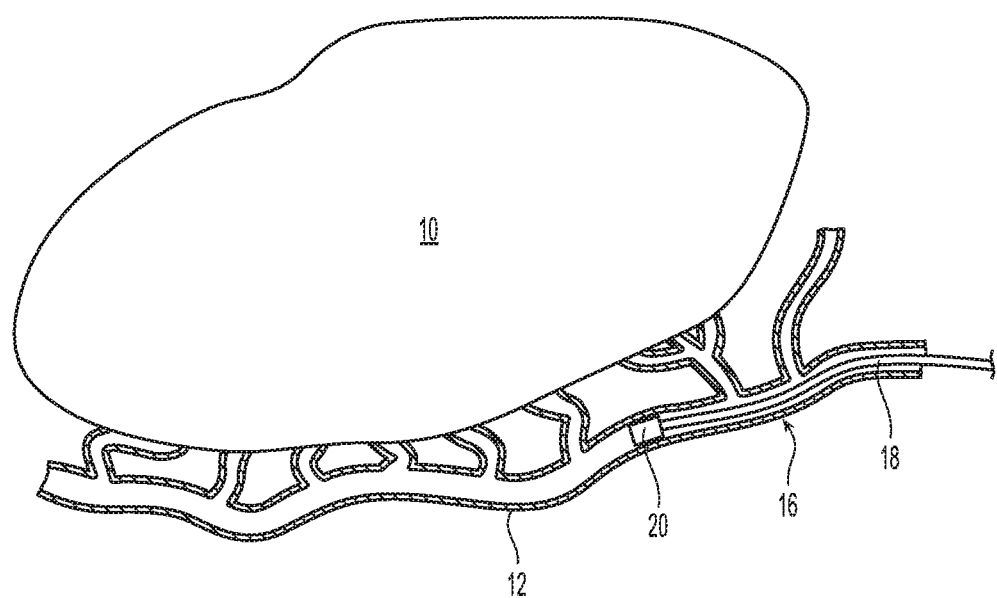
FIG. 1D is a partial, cross-sectional view illustrating an ovarian denervation technique in accordance with one aspect of the present disclosure.

FIG. 1D is a cross-sectional view illustrating denervation at a treatment location within the ovarian artery 12. As shown in FIG. 1D, a treatment device 16 including a shaft 18 and an end effector 20 supported thereon, can be extended toward the ovarian artery 12 to locate the end effector 20 at the treatment location within the ovarian artery 12. The end effector 20 can be configured for denervation at the treatment location via a suitable treatment modality, e.g., direct heat, electrode-based, microwave, light, ultrasonic, or another suitable treatment modality.

With continued reference to FIGS. 1A-1D, the treatment location can be proximate (e.g., at or near) a vessel or chamber wall (e.g., a wall of an ovarian artery, an ovarian vein, and/or another suitable structure), and the treated tissue can include tissue proximate the treatment location. For example, with regard to the ovarian artery 12, a treatment procedure can include ablating nerves in the ovarian plexus, which lay at least partially within or adjacent to the adventitia of the ovarian artery. In some embodiments, it may be desirable to disrupt ovarian nerves from a treatment location within a tubular structure or vessel and in close proximity to an ovary, e.g., closer to the ovary 10 than to a trunk of the vessel. This can increase the likelihood of disrupting nerves specific to the ovary, while decreasing the likelihood of disrupting nerves that extend to other organs. Vessels can decrease in diameter and become more tortuous as they extend toward an ovary 10. Accordingly, disrupting ovarian nerves from a treatment location in close proximity to an ovary can include using a device (e.g., treatment device 16) having size, flexibility, torque-ability, kink resistance, and/or other characteristics suitable for accessing narrow and/or tortuous portions of vessels.

Energy delivery techniques, such as an electrode-based approach, for example, can be used for ovarian denervation. Electrode-based treatment can include delivering electrical energy and/or another form of energy to tissue and/or heating tissue at a treatment location in a manner that disrupts neural function. For example, sufficiently disrupting at least a portion of a sympathetic ovarian nerve can slow or potentially block conduction of neural signals to produce a prolonged or permanent reduction in sympathetic activity. Some suitable energy modalities can include, for example, RF energy (monopolar and/or bipolar), pulsed RF energy, microwave energy, ultrasound energy (e.g., intravascularly delivered ultrasound, extracorporeal ultrasound, HIFU), laser energy, optical energy, magnetic energy, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are described in U.S. Patent Application Publication No. 2012/0116382, and incorporated herein by reference in its entirety. Other suitable devices and technologies, such as thermal devices, are described in U.S. Patent Application Publication No. 2012/0136350, also incorporated herein by reference in its entirety.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.), but less than about 45° C. for non-ablative thermal alteration, or the target temperature can be about 45° C. or higher kw ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For instance, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other aspects can include heating tissue to a variety of other suitable temperatures.

In some aspects of the present disclosure, a treatment procedure can include applying a suitable treatment modality at a treatment location in a testing step followed by a treatment step. The testing step, for example, can include applying the treatment modality at a lower intensity and/or fix a shorter duration than during the treatment step. This can allow an operator to determine (e.g., by neural activity sensors and/or patient feedback) whether nerves proximate the treatment location are suitable for denervation. Performing a testing step can be particularly useful for treatment procedures in which targeted nerves are closely associated with nerves that could cause undesirable side effects if disrupted during a subsequent treatment step.

In accordance with the present technology, denervation of a left and/or right ovarian nerve (e.g., ovarian plexus), which is intimately associated with a left and/or right ovarian artery 12 (FIG. 1C), may be achieved through intravascular access.

The following discussion provides further details regarding pertinent patient anatomy and physiology. This section is intended to supplement and expand upon the previous discussion regarding the relevant anatomy and physiology, and to provide additional context regarding the disclosed technology and the benefits associated with ovarian denervation.

Figure 2:
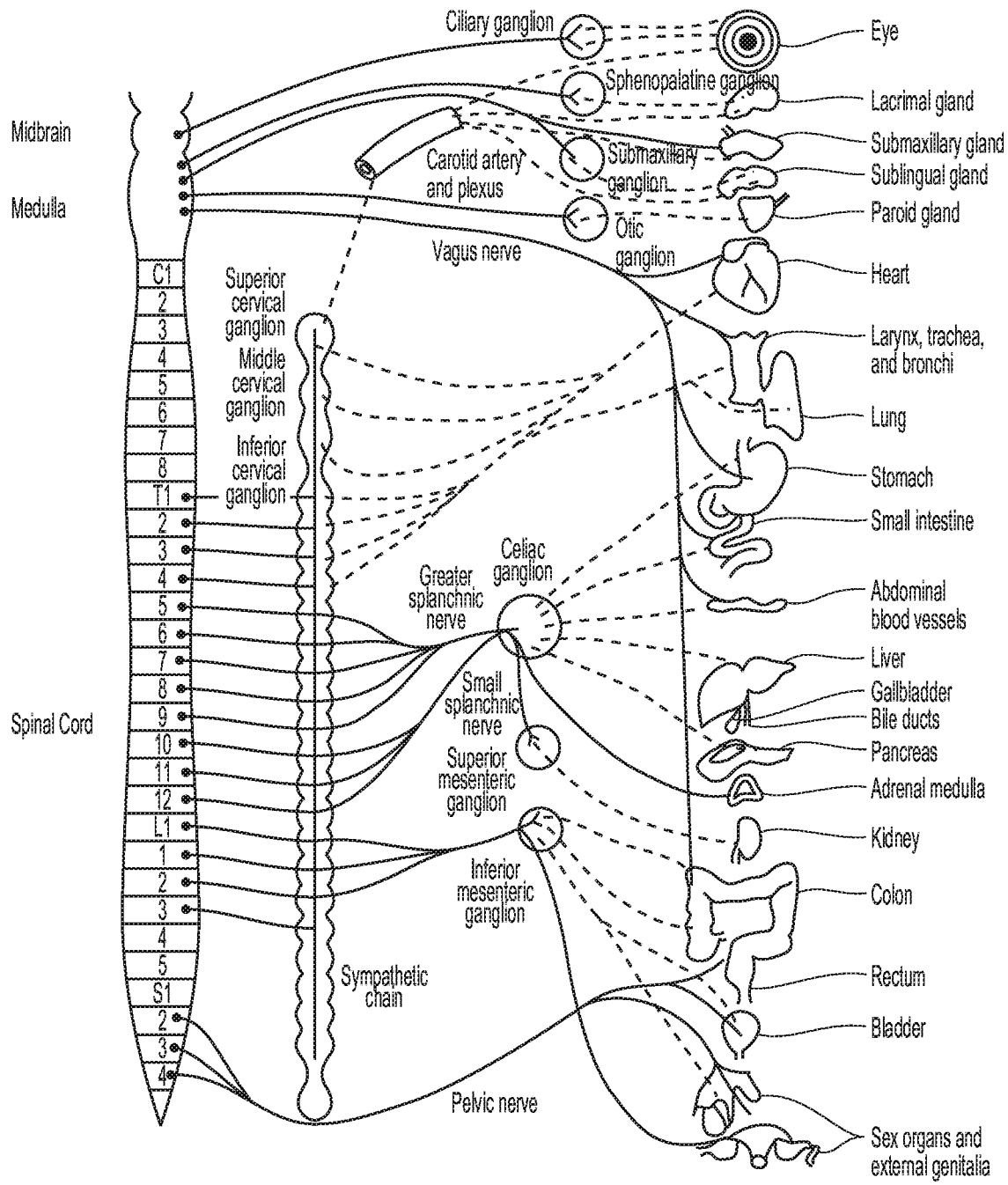
FIG. 2 is a conceptual illustration of a sympathetic nervous system (SNS) and how a brain communicates with a body via the SNS.

With reference to FIG. 2, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

The Sympathetic Chain

As shown in FIG. 2, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

Innervation of the Ovaries

Figure 3:
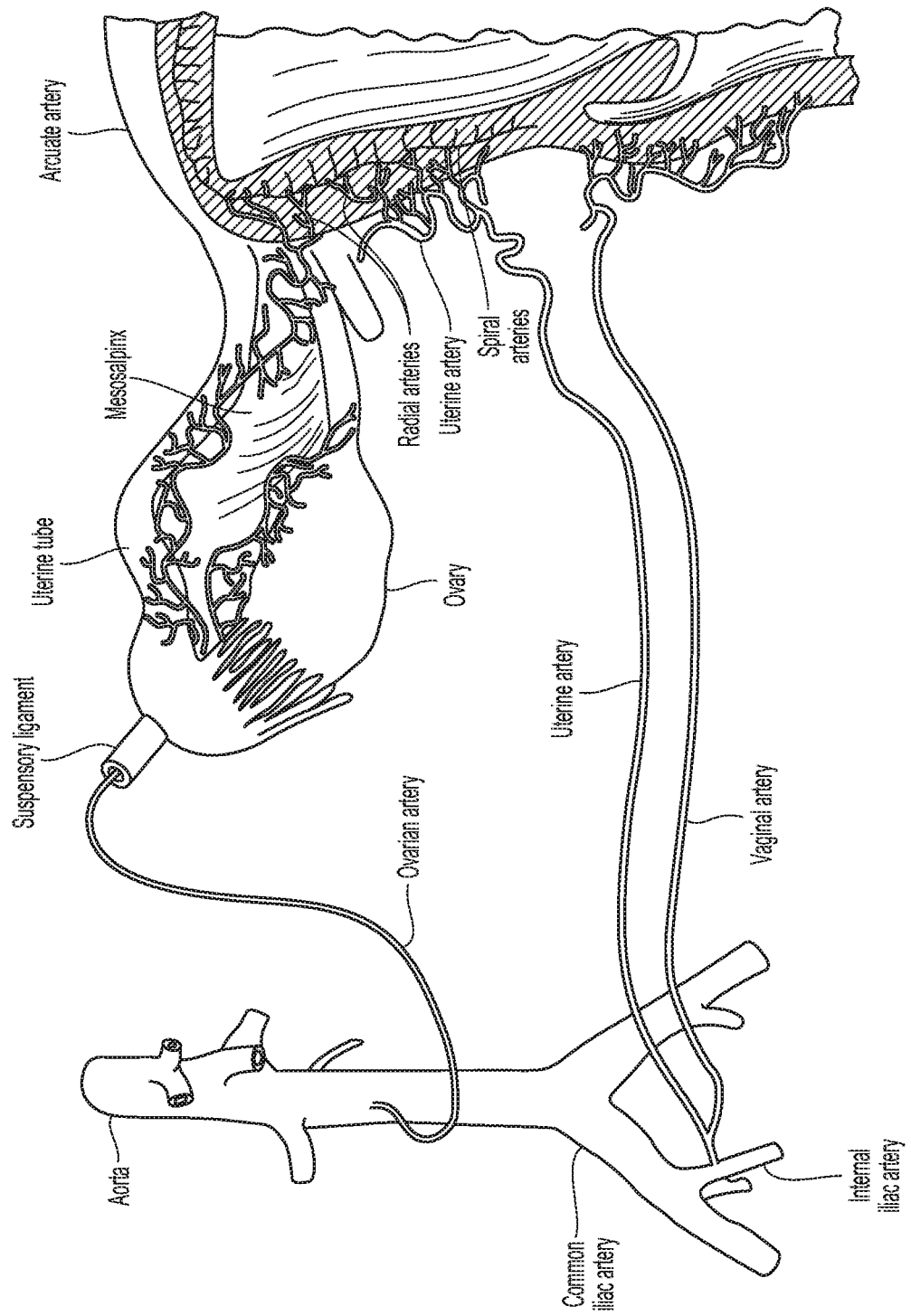
FIG. 3 is an enlarged anatomic view of arterial vasculature anatomy of an ovary.

The ovaries and part of the fallopian tubes and broad ligament of the uterus are innervated by the ovarian plexus, a network of nerve fibers accompanying the ovarian vessels and derived from the aortic and renal plexuses. As FIG. 3 shows, the blood supply to the ovary is provided by the ovarian artery. The ovarian plexus is an autonomic plexus that surrounds the ovarian artery and is carried in the suspensory ligament. The ovarian plexus extends along the ovarian artery until it arrives at the substance of the ovary. Fibers contributing to the ovarian plexus arise from the renal plexus, celiac ganglion, the superior mesenteric ganglion, the aorticorenal ganglion and the aortic plexus. The ovarian plexus, also referred to as the ovarian nerve, is predominantly comprised of sympathetic nerve fibers.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus, which are distributed to the renal vasculature, and give rise to the ovarian plexus which is distributed to the ovary and the fundus of the uterus.

Ovarian Sympathetic Neural Activity

Messages trawl through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAM) has been a longstanding, but somewhat ineffective, approach for reducing overactivity of the SNS.

For a more detailed description of pertinent patient anatomy and physiology, reference may be made to U.S. Patent Application Publication No. 2015/0051594, filed Mar. 7, 2013, the entire contents of which are incorporated herein by reference.

The presently disclosed systems, devices, and methods/techniques disrupt the nervous supply to the ovaries in order to control (e.g., down-regulate) ovarian hormonal secretion and treat hormonally-regulated diseases such as POCS and PMDD. By disrupting the ovarian nerve supply, hormonal overproduction leading to disease states may be effectively treated.

Figure 4:
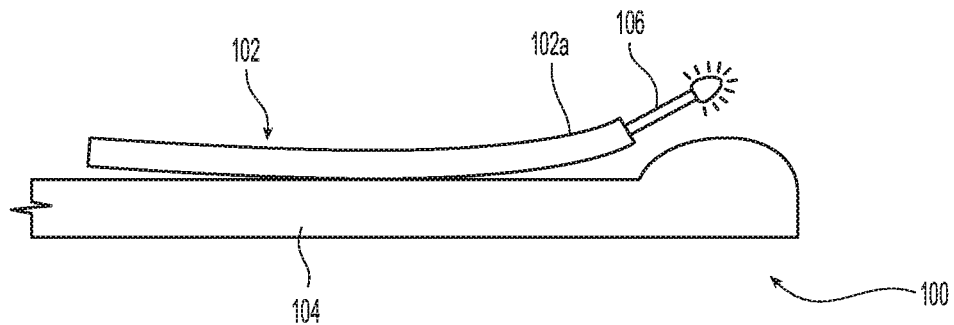
FIG. 4 is a side view of an ovarian denervation system in accordance with an illustrative embodiment of the present disclosure.
Figure 5A:
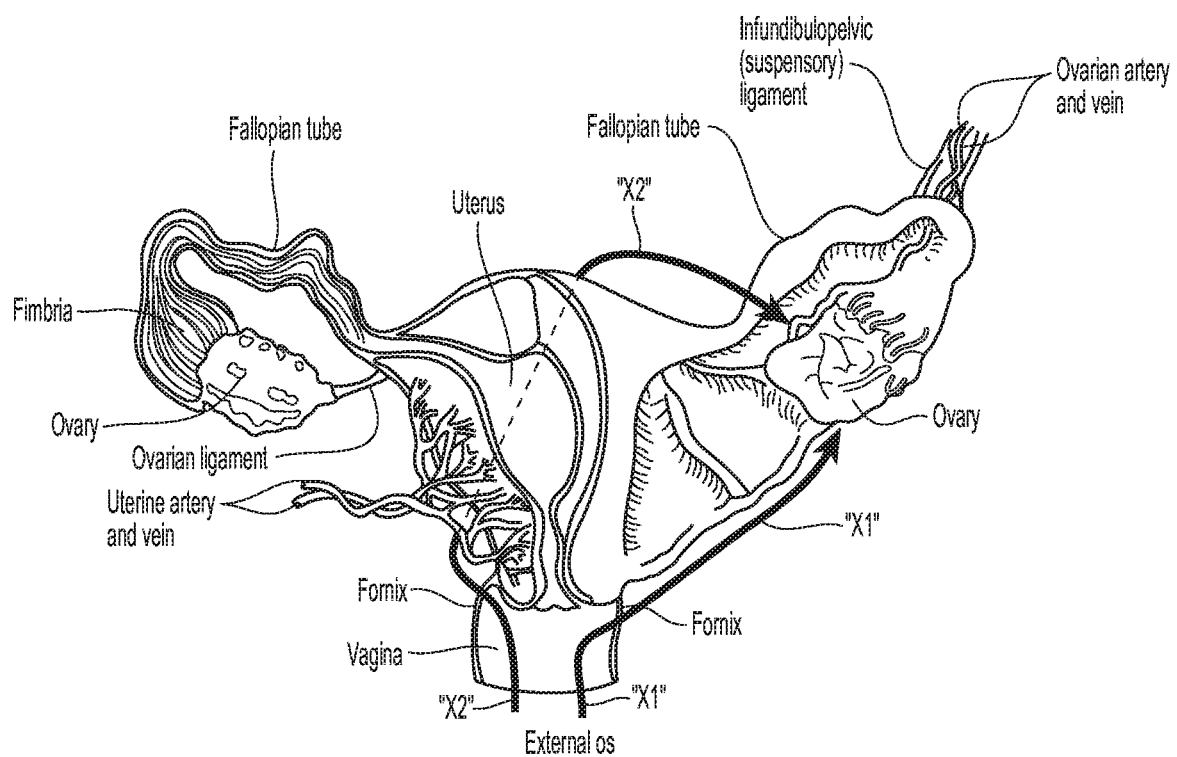
FIG. 5A is an anatomical view of vaginal tissue including illustrations of projected trajectories of components of the ovarian denervation system of FIG. 4 in accordance with an aspect of an ovarian denervation technique of the present disclosure.
Figure 5B:
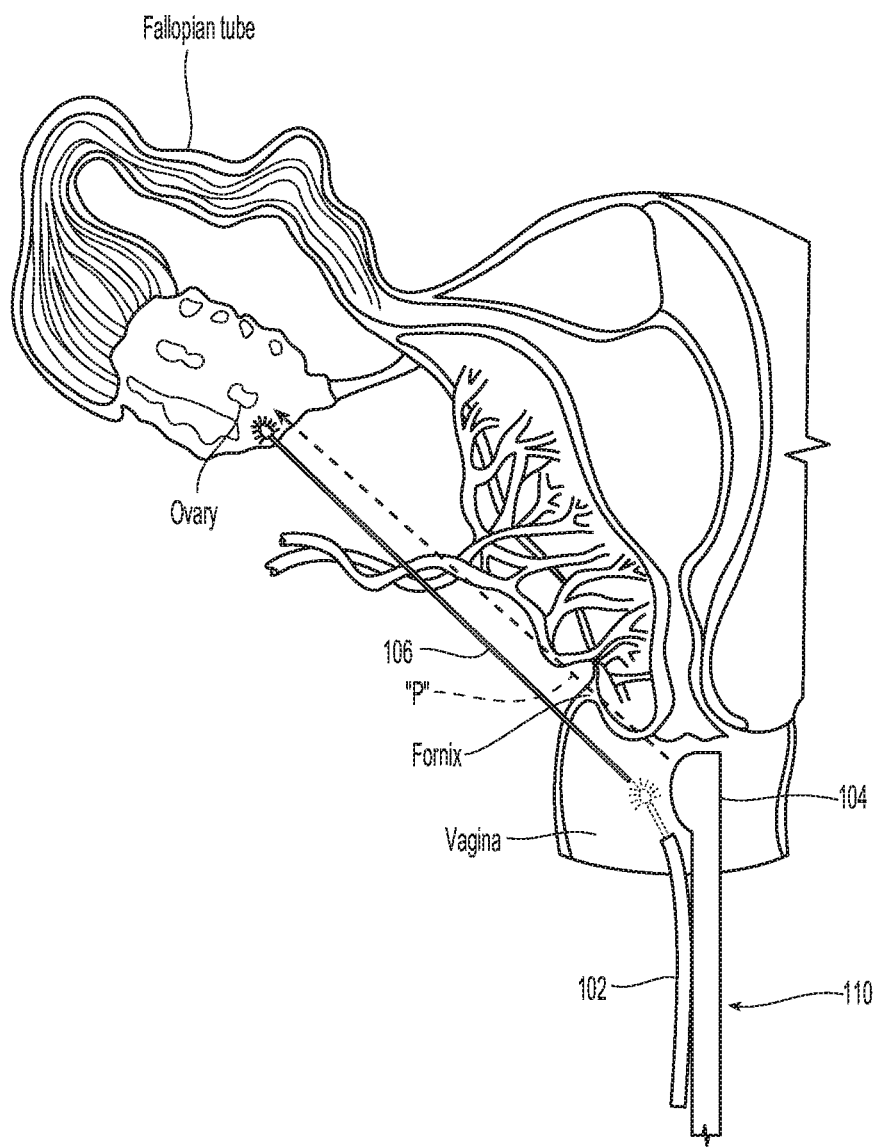
FIG. 5B is a schematic view illustrating an aspect of the ovarian denervation technique of FIG. 5A.

Turning now to FIGS. 4, 5A, and 5B, an ovary denervation system 100, in accordance with one embodiment of the present disclosure, includes a guide tube 102 secured to a transvaginal ultrasound probe 104, and a disruptor 106 (e.g., an ablation device) that is selectively advanceable relative to guide tube 102 (e.g., therethrough). Guide tube 102 is positioned to guide disruptor 106 toward the ovary so that disruptor 106 is maintained in alignment with a plane "P" of ultrasound projected from transvaginal ultrasound probe 104. Guide tube 102 may have a curved distal portion 102a that curves away from transvaginal ultrasound probe 104 to guide or otherwise direct disruptor 106 toward the ovary as disruptor 106 is advanced through guide tube 102. Once disruptor 106 is positioned adjacent to ovarian anatomy, disruptor 106 can be activated to disrupt (e.g., ablate) ovarian nerves. For a more detailed description of example disruptors, such as microwave ablation devices, reference can be made to U.S. Pat. Nos. 9,247,992, 9,119,650, or U.S. Patent Application Publication No. 2013/0317495, the entire contents of each of which are incorporated herein by reference. As used herein, the term "ablation device" may refer to any device that ablates tissue through direct application of heat, cooling, electrosurgical current, ultrasonic vibration, other energy transfer, etc., or combinations thereof.

As seen in FIG. 5A, a method for ovarian denervation includes inserting disruptor 106 into the ovaries and/or surrounding tissue through the vagina and vaginal fornix (see, for example, paths "X1" and "X2" illustrating the trans-fornix approach) under direct ultrasound guidance, for example, from transvaginal ultrasound probe 104 supported within the vagina. Transvaginal ultrasound probe 104 can be positioned within the vagina to project ultrasound through vaginal anatomy toward the ovary to enable visualization and facilitate positioning of disruptor 106 relative to ovaries, ovarian nerves, etc. so that disruptor 106 can be accurately positioned to disrupt the ovarian nerve supply upon application thereof. This trans-fornix approach may be similar to the manner in which an oocyte retrieval needle is placed into the ovary during IVF egg retrieval.

Figure 6:
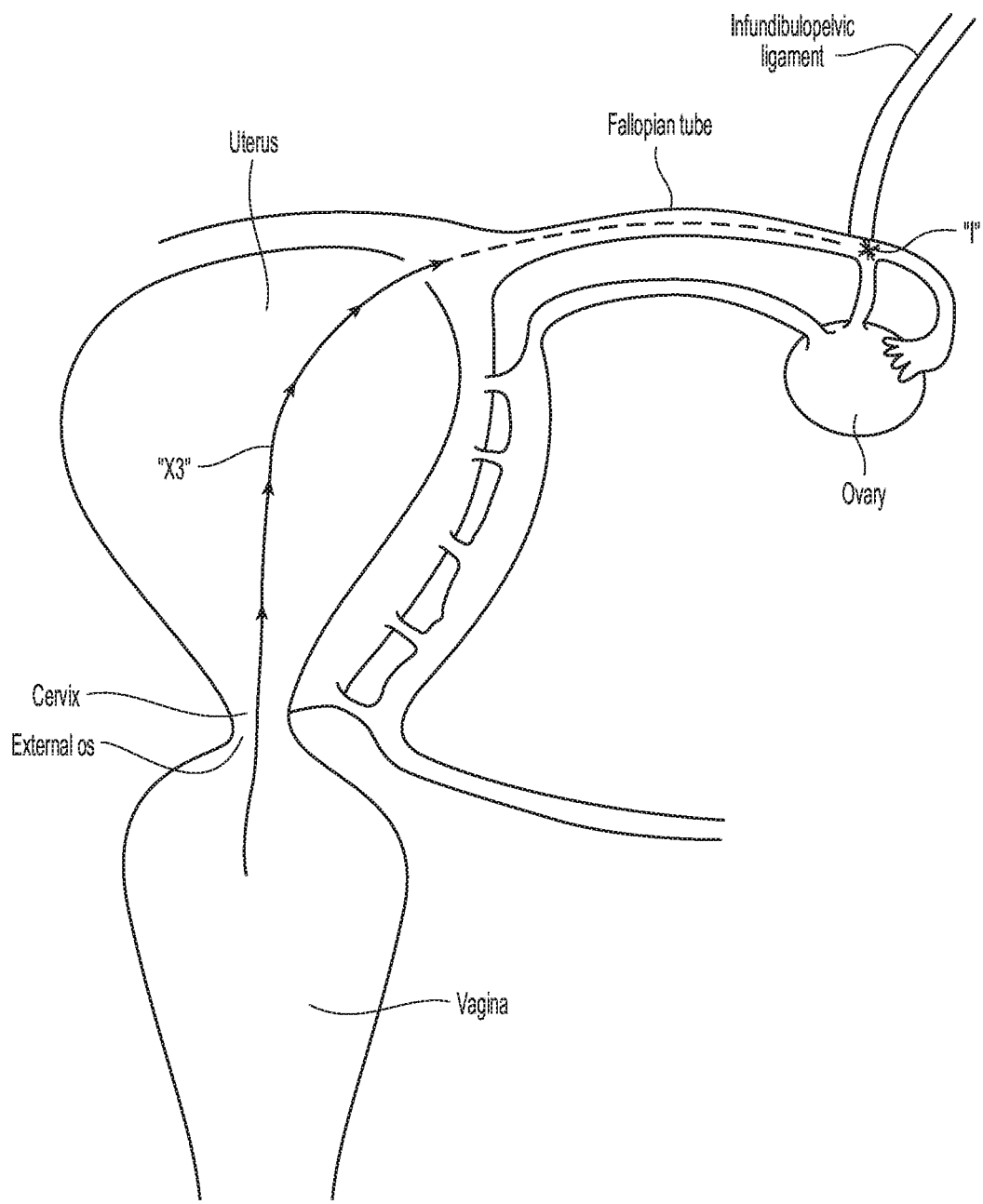
FIGS. 6-10 are views illustrating different ovarian denervation techniques in accordance with various aspects of the present disclosure.

With reference to FIG. 6, according to another aspect of the present disclosure, one method for ovarian denervation includes passing a disruptor (e.g., disruptor 106) along a path or trajectory "X3" that extends through the cervix and into the fallopian tubes so as to define a trans-fallopian approach. The disruptor is advanced to a location "I" where the infundibulopelvic ligament passes across and adjacent to the respective fallopian tube. Once the disruptor is in position at location "I," the disruptor can be applied to effectuate local treatment, for instance, by ablating ovarian nerves contained within the infundibulopelvic ligament. To facilitate visualization, any suitable guidance technique may be utilized to confirm disruption (e.g., ablation) is occurring at the desired location along the fallopian tube. For example, such guidance techniques may include ultrasound (e.g., transvaginal ultrasound probe 104 seen in FIG. 4), fluoroscopy, etc., or combinations thereof.

With continued reference to FIG. 6, in some aspects of the present disclosure, one or more of the presently disclosed systems and/or devices (e.g., the disruptor 106) may be advanced through (e.g., via piercing, puncturing, etc.) the fundus of the patient's uterus to access the infundibulopelvic ligament and/or ovarian nerves thereof, for example, in addition to, and/or instead of, through the fallopian tubes.

Figure 7:
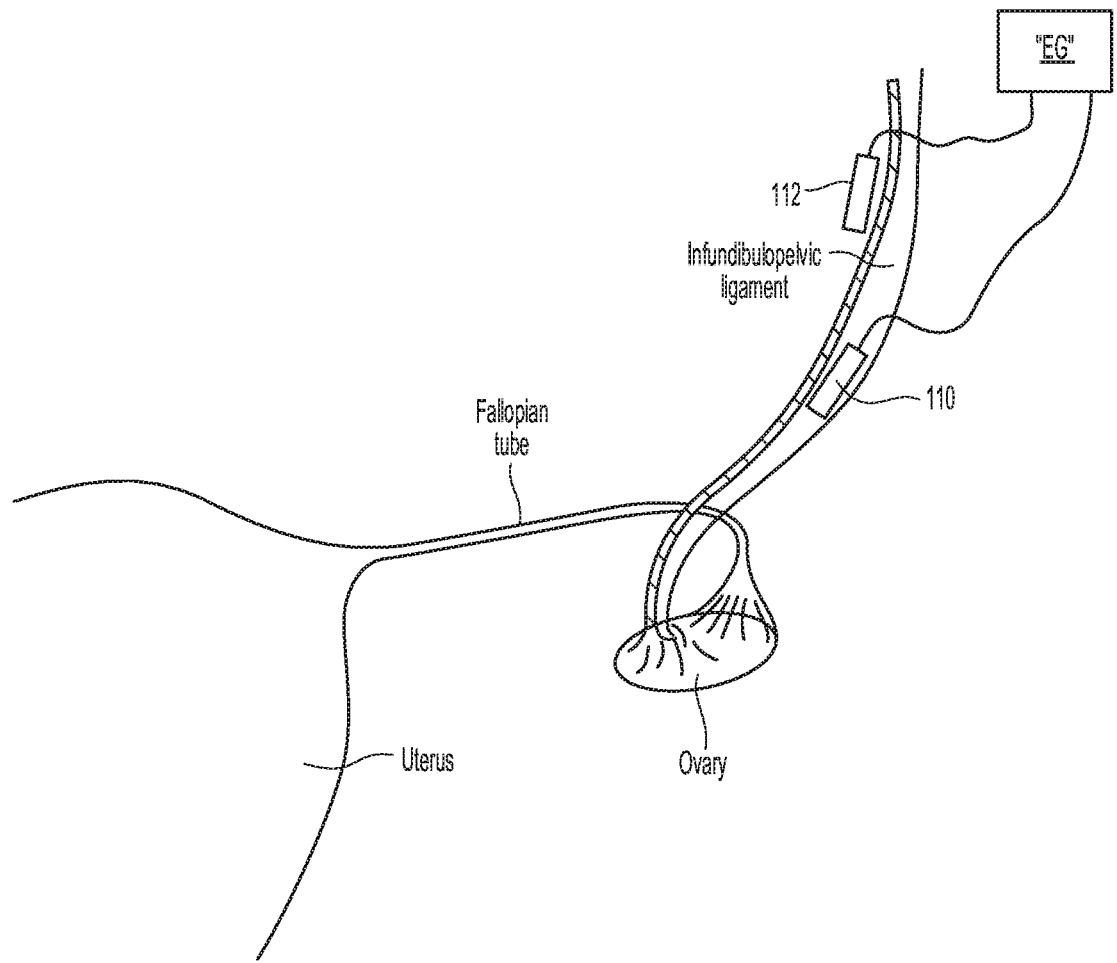

Turning now to FIG. 7, in one aspect of the present disclosure, another method for ovarian denervation includes positioning (temporarily or permanently implanting) disruptors, such as one or more electrodes 110, 112, within (e.g., electrode 110), and/or adjacent to (e.g., electrode 112), the ovarian artery for acting on the ovarian nerve supply. Electrodes 110, 112 are configured to be activated to apply electrical stimulus (e.g., electrical energy) to tissues/nerves of the infundibulopelvic ligament, effectively disrupting the sympathetic nerve signals transmitted through the ovarian nerves. The implanted electrodes 110, 112 may be configured to apply electrical stimulus continuously or intermittently. The electrical stimulus may be modulated, depending on the severity of symptom or phase of the patient's menstrual cycle. Electrodes 110, 112 may be coupled to an energy source such as an electrosurgical generator "EG" that selectively transmits electrical energy to electrodes 110, 112. For a more detailed description of one example of an electrosurgical generator, reference can be made to U.S. Pat. No. 8,784,410, the entire contents of which are incorporated by reference herein.

Figure 8:
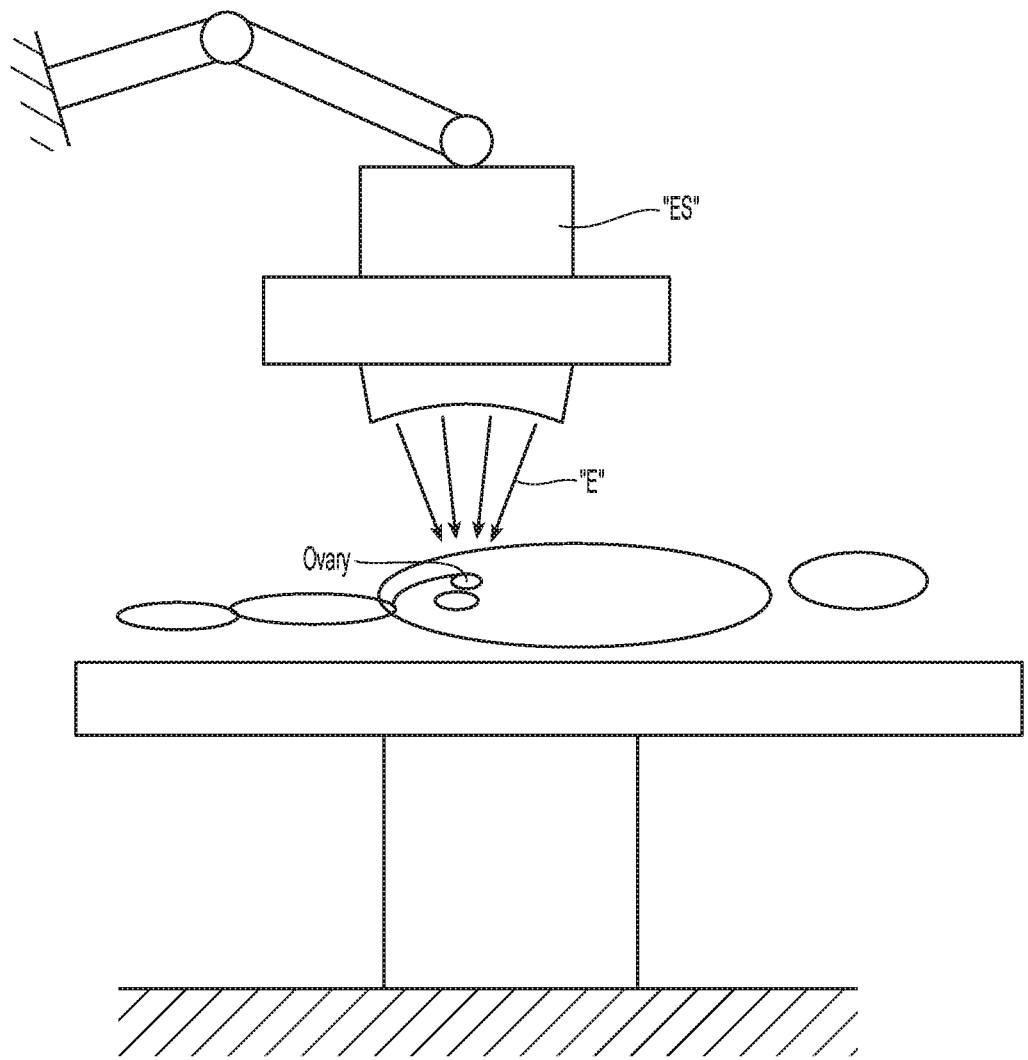

With reference to FIG. 8, according to a further aspect of the present disclosure, one method for ovarian denervation includes providing an energy source "ES" outside a patient and positioning the energy source "ES" so as to enable application of focused energy "E" to the ovary, the tissues surrounding the ovary, and/or the ovarian vessel (e.g., artery), in order to disrupt the nerve supply. Any suitable energy application technique may be utilized and may be applied directly (e.g., such that target site is externally exposed) or indirectly (e.g., such that the target site is not externally exposed and energy is required to pass through other tissue first). For example, the energy source "ES" can be configured to provide focused ultrasound, focused radiation (e.g., gamma-knife), focused microwave energy, light, etc., or combinations thereof. The energy source "ES" may include a cyclotron, a linear accelerator, a kilovoltage unit, a teletherapy unit, etc., or combinations thereof.

Figure 9:
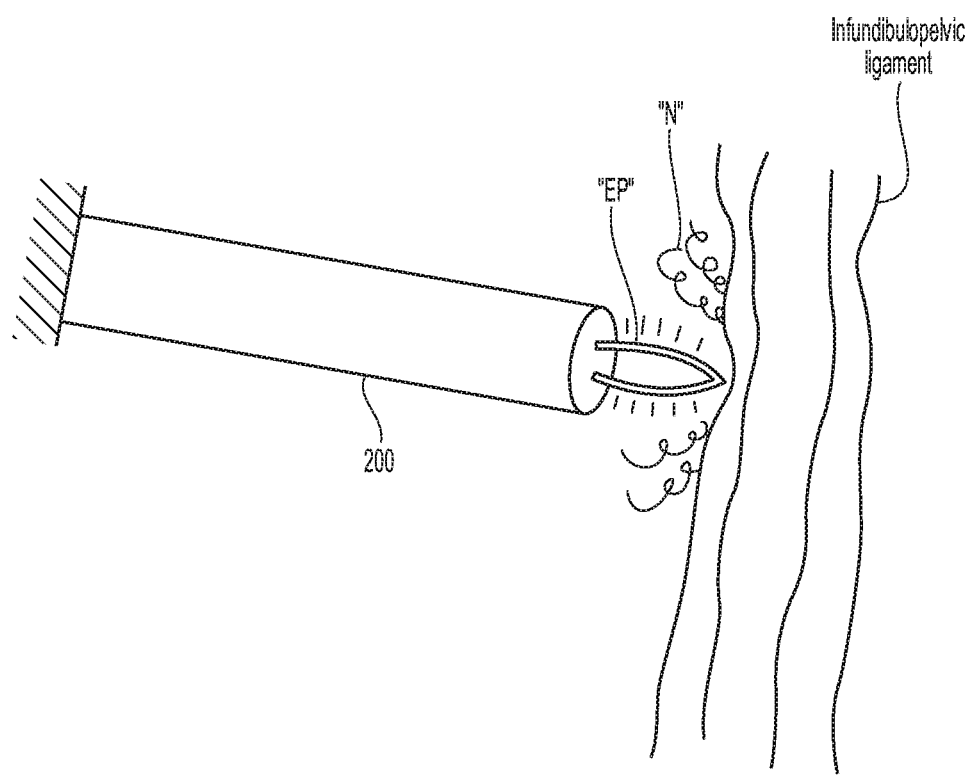

Referring now to FIG. 9, in yet another aspect of the present disclosure, a method for ovarian denervation includes applying a beam of electrosurgical plasma "EP," from a disruptor such as a plasma emitter 200 (e.g., an argon plasma emitter), to a surface of the infundibulopelvic ligament to ablate the sympathetic nerves "N" running along the outer surface of the ovarian artery for denervating the ovarian nerve supply. For a more detailed description of an example of plasma emitter, reference can be made to U.S. Pat. No. 6,039,736, the entire contents of which are incorporated herein by reference.

According to another aspect of the present disclosure, one method for ovarian denervation includes applying light at a controlled frequency (e.g., photoablation with a laser), with a disruptor such as a light emitting instrument (not shown), to the tissues of the infundibulopelvic ligament (see FIGS. 1A, 9) or to the tissue surrounding the ovary to ablate ovarian nerve tissue. For example, photoablation with a laser (e.g. an excimer or exiplex laser) having a wavelength of approximately 200 nm may be used to disrupt ovarian nerves. With a controlled frequency of light, more energy can be absorbed by nerve tissue than by other surrounding tissue so that the nerves are locally ablated with minimal surrounding tissue damage.

Figure 10:
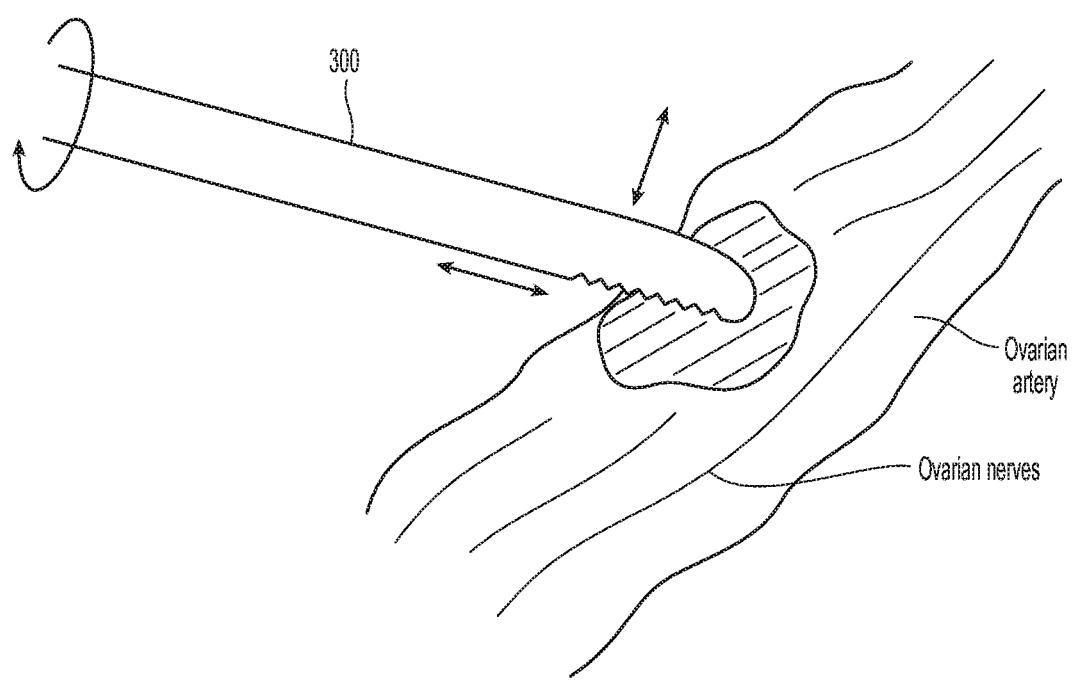

Turning now to FIG. 10, in still another aspect of the present disclosure, one method for ovarian denervation includes applying a disruptor such as a mechanical resection device (e.g., a scalpel) or shaver blade 300 to the surface of the ovarian artery to denervate (e.g., mechanically disrupt and resect) the ovarian nerves at the outer surface of the ovarian artery (e.g., by cutting and/or scraping).

Figure 11A:
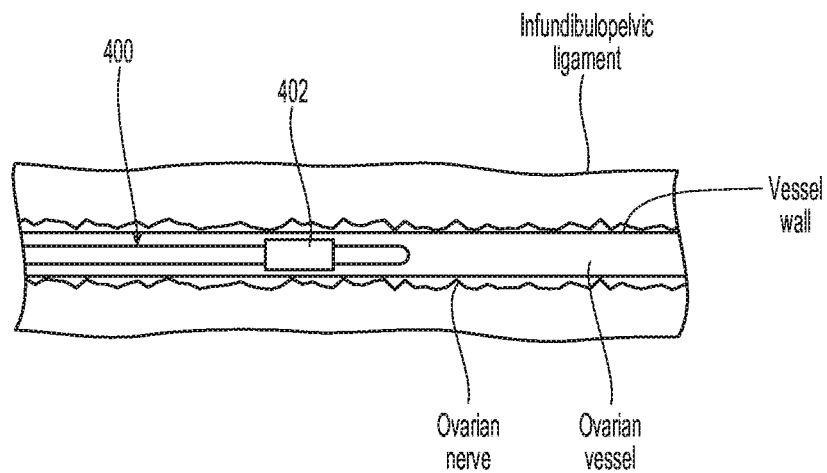
FIGS. 11A and 11B are progressive views illustrating an ovarian denervation technique involving a balloon catheter in accordance with an aspect of the present disclosure.
Figure 11B:
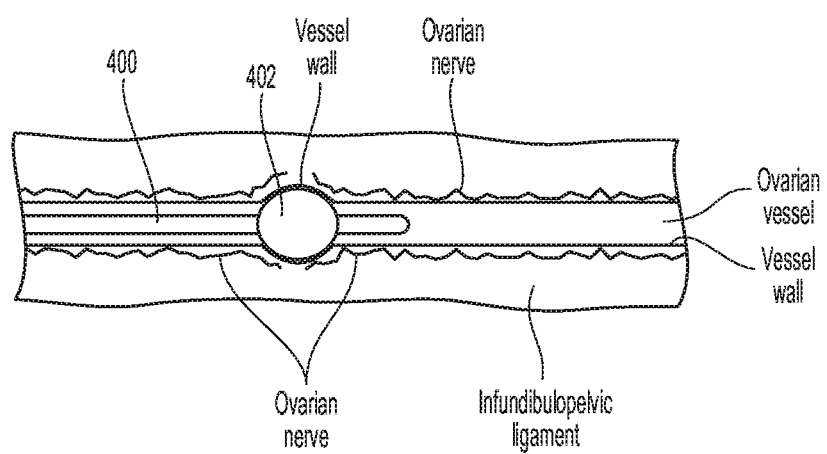

As seen in FIGS. 11A and 11B, in one aspect of the present disclosure, still another method for ovarian denervation includes introducing a disruptor, in the form of a balloon catheter 400, into one or more ovarian vessels within the infundibulopelvic ligament. A balloon 402 of balloon catheter 400 can be inflated with inflation fluid (e.g., saline) from an inflation source (not shown) coupled to balloon catheter 400. In particular, balloon 402 can be selectively inflated within an ovarian vessel to a threshold volume so that the ovarian vessel wall expands an amount sufficient to mechanically tear or disrupt one or more nerves running along the ovarian vessel without causing the wall of the ovarian vessel to tear. Balloon 402 may then be deflated so that balloon catheter 400 can be withdrawn. Although described with respect to a balloon, any suitable expandable structure can be utilized (e.g., a stent, radially extendable prongs, etc.). The expandable structure (e.g., balloon 402) may be deflated and/or re-inflated as desired, for example, to repeat the technique at one or more additional locations along the vessel or in another vessel. For a more detailed description of an example of balloon catheter, reference can be made to U.S. Patent Application Publication No. 2014/0250661, the entire contents of which are incorporated herein by reference.

Figure 12A:
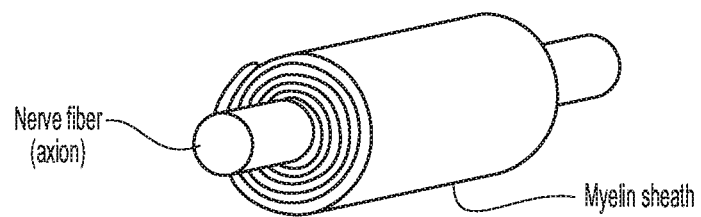
FIGS. 12A-12B are anatomical views of nerve fiber and its myelin sheath in a normal state.
Figure 12B:
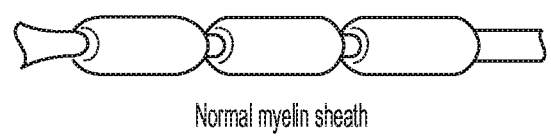
Figure 12C:
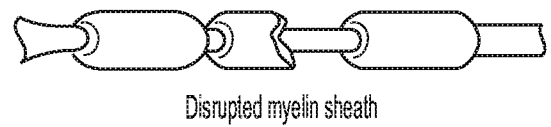
FIG. 12C is an anatomical view of the nerve fiber and its myelin sheath in a disrupted state.

As seen in FIGS. 12A-12C, in certain aspects of the present disclosure, the myelin sheath surrounding the ovarian nerves may be disrupted, for example, with the disruptor 106 (or utilizing any of the other presently disclosed devices, systems, and/or techniques), to effectuate ovarian denervation.

Any of the presently disclosed techniques can be effectuated individually or in any suitable combination.

The various embodiments/techniques disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method for effectuating ovarian denervation, the method comprising:
   fixedly implanting at least one electrode within a portion of an ovarian vessel within an infundibulopelvic ligament of a person;
   fixedly implanting at least one additional electrode adjacent the ovarian vessel and adjacent the infundibulopelvic ligament of the person; and
   activating the at least one electrode and the at least one additional electrode after fixedly implanting the at least one electrode and the at least one additional electrode to disrupt an overactive ovarian nerve by applying an intermittent electrical signal to the overactive ovarian nerve to provide a therapeutic treatment to the overactive ovarian nerve, wherein the at least one additional electrode is activated through a wired connection extending into the infundibulopelvic ligament of the person, and
   wherein the at least one electrode and the at least one additional electrode remain fixedly implanted for at least a duration of the therapeutic treatment provided to the overactive ovarian nerve.

2. The method of claim 1, wherein activating the at least one additional electrode includes intermittently conducting electrical energy through the at least one additional electrode to disrupt sympathetic nerve signals of the overactive ovarian nerve.

3. The method of claim 1, wherein activating the at least one electrode includes intermittently passing electrical energy through the at least one electrode to disrupt sympathetic nerve signals of the overactive ovarian nerve.

4. The method of claim 3, wherein activating the at least one additional electrode includes intermittently passing electrical energy through the at least one additional electrode to disrupt sympathetic nerve signals of the overactive ovarian nerve.

5. The method of claim 1, wherein the intermittent electrical signal is applied to the at least one electrode and the at least one additional electrode from an electrosurgical generator positioned outside a body of the person.

6. The method of claim 5, wherein the at least one electrode is connected to the electrosurgical generator by a second wired connection and the at least one additional electrode is connected with the electrosurgical generator by the wired connection separate from the second wired connection, and wherein the electrosurgical generator applies electrical energy to the at least one electrode through the second wired connection and the electrosurgical generator applies electrical energy to the at least one additional electrode through the wired connection.

7. A method for effectuating ovarian denervation, the method comprising:
   fixedly implanting at least one electrode within a portion of an ovarian vessel within an infundibulopelvic ligament of a person;
   fixedly implanting at least one additional electrode adjacent the infundibulopelvic ligament of the person; and
   activating the at least one electrode or the at least one additional electrode after fixedly implanting the at least one electrode or the at least one additional electrode to disrupt an overactive ovarian nerve by applying an intermittent electrical signal to the overactive ovarian nerve to provide a therapeutic treatment to the overactive ovarian nerve, wherein the at least one additional electrode is activated through a wired connection extending into the infundibulopelvic ligament of the person, and
   wherein the at least one electrode and the at least one additional electrode remain fixedly implanted for at least a duration of the therapeutic treatment provided to the overactive ovarian nerve.

8. The method of claim 7, wherein activating the at least one additional electrode includes intermittently conducting electrical energy through the at least one additional electrode to disrupt sympathetic nerve signals of the overactive ovarian nerve.

9. The method of claim 7, wherein activating the at least one electrode includes intermittently passing electrical energy through the at least one electrode to disrupt sympathetic nerve signals of the overactive ovarian nerve.

10. The method of claim 9, wherein activating the at least one additional electrode includes intermittently passing electrical energy through the at least one additional electrode to disrupt sympathetic nerve signals of the overactive ovarian nerve.

11. The method of claim 7, wherein the intermittent electrical signal is applied to the at least one electrode and the at least one additional electrode from an electrosurgical generator positioned outside a body of the person.

12. The method of claim 11, wherein the at least one electrode is connected to the electrosurgical generator by a second wired connection and the at least one additional electrode is connected with the electrosurgical generator by the wired connection separate from the second wired connection, and wherein the electrosurgical generator applies electrical energy to the at least one electrode through the second wired connection and the electrosurgical generator applies electrical energy to the at least one additional electrode through the wired connection.

* * * * *